United States Patent [19]

Macher

[11] Patent Number: 5,219,843

[45] Date of Patent: Jun. 15, 1993

[54] SACCHARIDE DERIVATIVES

[75] Inventor: Ingolf Macher, Breitenbach, Austria

[73] Assignee: Sandoz Ltd., Basel, Switzerland

[21] Appl. No.: 798,304

[22] Filed: Nov. 22, 1991

Related U.S. Application Data

[63] Continuation of Ser. No. 515,291, Apr. 27, 1990, abandoned, which is a continuation of Ser. No. 396,874, Aug. 22, 1989, abandoned, which is a continuation of Ser. No. 247,970, Sep. 22, 1988, abandoned.

[30] Foreign Application Priority Data

Sep. 23, 1987 [DE] Fed. Rep. of Germany ....... 3731953

[51] Int. Cl.$^5$ ................. A61K 31/70; C07H 11/04; C07H 5/06
[52] U.S. Cl. ............................ 514/62; 514/23; 536/117; 536/17.2; 536/17.4; 536/17.9; 536/55.2
[58] Field of Search .................... 536/117, 17.2, 17.4, 536/17.9, 55.2; 514/62, 42, 23

[56] References Cited

U.S. PATENT DOCUMENTS 4,698,331 10/1987 Macher et al. ............. 536/17.2

FOREIGN PATENT DOCUMENTS 180895 7/1989 Japan.
86/05687 10/1986 World Int. Prop. O.

Primary Examiner—Johnnie R. Brown
Assistant Examiner—Everett White
Attorney, Agent, or Firm—Robert S. Honor; Melvyn M. Kassenoff; Thomas O. McGovern

[57] ABSTRACT

The saccharides of formula I,

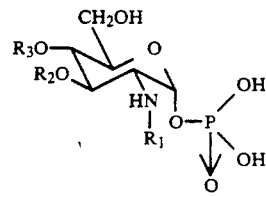

wherein
$R_1$, $R_2$ and $R_3$ independently are optionally substituted acyl, are novel. They possess interesting pharmacological, especially immunostimulant, antiinflammatory and antitumor properties. They may be obtained by deprotection of a corresponding compound in protected form.

4 Claims, No Drawings

SACCHARIDE DERIVATIVES

This is a continuation of application Ser. No. 07/515,291, filed Apr. 27, 1990, which in turn is a continuation of application Ser. No. 07/396,874, filed Aug. 22, 1989, which in turn is a continuation of application Ser. No. 07/247,970, filed Sep. 22, 1988, all of which are now abandoned.

The present invention relates to new saccharide derivatives, namely new α-D-glucopyranose derivatives.

The invention comprises the compounds of formula I

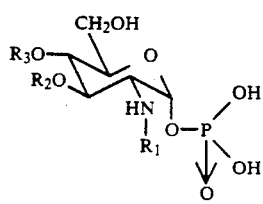

I wherein
$R_1$, $R_2$ and $R_3$ independently are optionally substituted acyl,
in free form or in salt form.

The ring structure has the configuration of α-D-glucopyranose.

Acyl preferably is alkylcarbonyl of altogether 4 to 20, preferably 12 to 16, especially 14 carbon atoms, which may optionally be monosubstituted in the 3 position by hydroxy or acyloxy, whereby the acyl part of acyloxy preferably has the significance indicated above as preferred for acyl and the carbon atom in the 3 position then may have the R or S configuration. In the corresponding compounds of formula I $R_1$, $R_2$ and $R_3$ may thus be in achiral form or in the R or S configuration. When they are in chiral form the R configuration is preferred.

The configuration remains unchanged when the processes described herein are effected, namely, when R, S or racemic compounds are used as starting material, the corresponding R, S, or, respectively, racemic compounds are obtained.

Acyl preferably is substituted.
Preferred substituent of acyl is hydroxy.
$R_1$, $R_2$ and $R_3$ preferably are identical.

A subgroup of compounds of formula I is the compounds of formula I wherein $R_1$, $R_2$ and $R_3$ are as defined above after formula I with the proviso that $R_2$ and $R_3$ are identical, in free form or in acid addition salt form. In this subgroup $R_1$ may or may not be identical to $R_2$ and $R_3$.

A further subgroup of compounds of formula I is the compounds of formula I wherein $R_1$, $R_2$ and $R_3$ are as defined above after formula I with the proviso that when $R_1$ is 3-hydroxydodecanoyl or 3-hydroxyhexadecanoyl, then at least one of $R_2$ and $R_3$ is other than dodecanoyl, 3-(R)-hydroxydodecanoyl or 3-(R)-hydroxy-dodec-5-cis-enoyl. In a subgroup thereof $R_1$, $R_2$ and $R_3$ are as defined above after formula I with the proviso that $R_1$ is other than 3-hydroxydodecanoyl or 3-hydroxyhexadecanoyl and $R_2$ and $R_3$ are other than dodecanoyl, 3-hydroxydodecanoyl or 3-hydroxy-dodec-5-enoyl.

A further subgroup of compounds of formula I is the compounds of formula I wherein $R_2$ and $R_3$ are as defined above after formula I and $R_1$ is alkylcarbonyl of altogether 4 to 20 carbon atoms optionally monosubstituted in the 3 position by hydroxy. In a subgroup thereof $R_1$ and $R_2$ are alkylcarbonyl of altogether 4 to 20 carbon atoms optionally monosubstituted in the 3 position by hydroxy. In a subgroup thereof $R_1$, $R_2$ and $R_3$ are alkylcarbonyl of altogether 4 to 20 carbon atoms optionally monosubstituted in the 3 position by hydroxy. In a subgroup thereof $R_1$, $R_2$ and $R_3$ are alkylcarbonyl of altogether 4 to 20 carbon atoms monosubstituted in the 3 position by hydroxy.

The structure of the compounds of the invention is somewhat related to that of lipid A of gram-(−)-bacteria and its monosaccharide precursor, lipid X, and to the compounds disclosed in e.g. the following publications:
Sandoz EP 180 608
WARF WO 86/05687
Sandoz WO 87/00174.

However, before the date of this invention, 2,3,4-triacylated glucosamines had never been described as components or derivatives of lipid A. The very broad and speculative formula disclosed on page 5 in WARF WO 86/05687 might be argued to encompass 2,3,4-tri- and 2,3,4,6-tetraacylated glucosamines but this disclosure provides no method to obtain such compounds, which do not occur naturally. The compounds of the present invention moreover possess particularly beneficial pharmacological properties.

The invention also provides a process for the preparation of a compound of formula I in free form or in salt form comprising deprotecting a corresponding compound of formula II

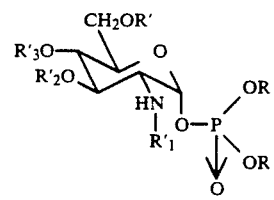

II wherein
R and R' are protecting groups and
$R_1'$, $R_2'$ and $R_3'$ have the significance indicated above for, respectively, $R_1$, $R_2$ and $R_3$ with the proviso that any hydroxy group therein is in protected from,
and recovering the resultant compound of formula I in free form or in salt form.

The process of the invention is a deprotection reaction. It may be effected in accordance with known methods. Depending on the nature of the protecting groups deprotection may be effected in one single step or in several successive steps. When the protecting groups are hydrogenolytically splittable groups such as benzyl or triphenylmethyl the deprotection may e.g. be effected hydrogenolytically, e.g. by hydrogenating over palladium on charcoal.

Indicated as protecting groups are protecting groups generally used in saccharide chemistry. R' may e.g. be the triphenylmethyl group. Indicated protecting groups R for the phosphate or hydroxy group are also generally known, e.g. benzyl.

The resultant compounds of formula I may be recovered from the reaction mixture and purified in accordance with known methods.

The compounds of formula I may be recovered in free form or in salt form. Preferred salt forms are e.g. salts with basic hydrophilic compounds such as tris(hydroxymethyl)aminomethane and L-lysine. Salt forms may be obtained from the free base forms in known manner, and vice-versa.

The compounds used as starting materials may be obtained in accordance with known procedures.

The compounds of formula II may be obtained e.g. by appropriately acylating corresponding compounds of formula III

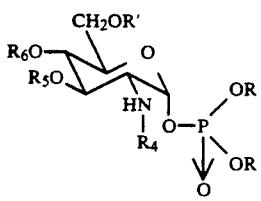

wherein
R and R' are as defined above and
$R_4$, $R_5$ and $R_6$ are hydrogen or have the significance indicated above for, respectively, $R_1$, $R_2$ and $R_3$ with the proviso that any hydroxy group therein is in protected form and the further proviso that at least one of $R_4$, $R_5$ and $R_6$ is hydrogen.

The acylation is preferably effected at a reduced temperature, e.g. at about 4° C. The reaction is preferably effected in an inert solvent such as a hydrocarbon, e.g. methylene chloride. The acylating agent may e.g. be supplemented with dicyclohexylcarbodiimide and 4-dimethylaminopyridine.

The compounds of formula III may be obtained e.g. starting from the compound of formula IV

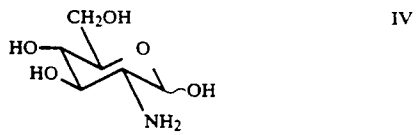

by appropriately protecting and substituting the OH and $NH_2$ groups therein using the methods generally known in the chemistry of saccharides. The choice of the protecting groups is effected depending on the position of the corresponding OH and $NH_2$ groups, while any OH or, respectively, $NH_2$ group which it is foreseen to acylate in the following step is left unprotected. A first acylation step to acylate e.g. the $NH_2$ and/or an OH group is followed by a deprotection step. The deprotection step is itself followed by a selective protection step leaving one or more OH groups unprotected. Subsequently acylation may again be effected, if appropriate with another acyl group. Repetition of similar reaction steps allows the preparation of compounds wherein the three acyl groups are different. In formula IV the configuration of the OH group in the 1 position is indifferent, introduction of the phosphate group leads to compounds having the configuration indicated in formula III at the corresponding position.

It should be noted that in any event for each acylation step the OH group in the 6 position must be protected since it is not intended to acylate it. The same also applies for the phosphate residue, which must be protected prior to each acylation step. The phosphate residue may e.g. be introduced by reaction of an organometallic compound such as butyl lithium with the compound of formula IV or a partially acylated derivative thereof optionally having the hydroxy group in position 6 in protected form, and thereafter adding e.g. dibenzylphosphorochloridate to the reaction mixture. The reaction with the organometallic compound preferably is effected in an inert solvent, e.g. in a cyclic ether such as tetrahydrofuran. The reaction temperature preferably is reduced, e.g. −50°C. The solvent is an aliphatic hydrocarbon such as hexan. The hydroxy groups of the phosphate residue are protected, e.g. by benzyl.

Insofar as the preparation of the starting materials is not particularly described herein, these are known or may be prepared in accordance with known procedures or in a manner analogous to known procedures, e.g. analogous to the procedures described in the Examples.

The compounds of formula I in free form or in pharmaceutically acceptable salt form, hereinafter referred to as the compounds of the invention, possess pharmacological activity. They are therefore useful as pharmaceuticals.

In particular, the compounds of the invention exert an effect on the unspecific antimicrobial resistance. This appears from e.g. the following tests:

1. Determination of endotoxic activity in the limulusamoebocytes lysate test.
2. Induction of endotoxin shock in the mouse.
3. Microbial septicemia in the neutropenic mouse (number of germs per mouse, e.g. *Pseudomonas aeruginosa* Δ12: about $6 \times 10^4$; *E. coli* Δ120: about $2 \times 10^6$; *Staph. aureus* Δ113: about $2 \times 10^6$; *Candida albicans* Δ124: about $2 \times 10^4$).

The compounds of the invention effect marked improvements in time and rate of survival over untreated infection controls in experimental infections with gramnegative agents (e.g. Pseudomonas and *E. coli*) as well as in infections with grampositive agents (e.g. *Staph. aureus*) or yeasts (e.g. *Candida albicans*), after parenteral administration.

4. Activation of the oxidative metabolism of human blood neutrophils.
5. Carbon clearance test.
6. Herpes infection in the mouse.

In the experimental HSV-1-infection, the compounds of the invention cause marked improvements as regards the course of illness, survival time and survival rate over untreated controls. These effects are observed after a single i.p. or s.c. administration between days 0 or −1 and +6.

7. CSF induction (colony-stimulating factor).

The compounds of the invention induce CSFs to various extents in mice, whereby time-kinetic differences in CSF-activities are also observed. These could be advantageous in therapeutic use.

8. Induction of Interleukin-1 (IL-1).

The compounds of the invention possess to various extents (in concentrations of 0.1–50 µg/ml) the capacity to induce IL-1 production in macrophages.

9. Induction of LPS-(endotoxin) tolerance (lethality tolerance).

The compounds of the invention are eliciting this tolerance already after single i.p. administration of 0.25 mg/mouse. Pretreated (tolerant) mice are exposed to a LPS-challenge at a dosage of 0.01 µg LPS+8 mg galactosamine/mouse i.p. at various times (1 day to 3 weeks) following the last treatment. A larger proportion of animals survive this LPS challenge, especially after repeated administration (3 times), as compared with challenge controls not pretreated.

Furthermore, the compounds of the invention possess antiinflammatory activity, especially in nonspecific, in immunologically-induced, and in hypersensitivity-induced inflammation and in allergic reactions.

This activity may be demonstrated by various test methods, e.g. by investigation of the influence on prostaglandin synthesis in vitro and in vivo. A marked inhibition of LPS- or zymosan-induced $PGE_2$-production is found. The inhibition of LPS-induced $PGE_2$-release by mouse peritoneal leucocytes after pretreatment with test substances is measured in vivo and a marked reduction in $PGE_2$-release is found as compared with controls.

In a further test, the influence on procoagulant activity (PCA) is measured.

The addition of test substance reduces the PCA elicited by LPS as compared to the control value as manifested by an increase in coagulation time. Pretreatment with test substance similarly results in reduction of PCA.

In vivo, the influence of LPS-induced PCA by mouse peritoneal leucocytes after pretreatment with test substance may be shown. The PCA of rabbit peritoneal leucocytes may be reduced after induction of the generalized Shwartzman reaction, and by pretreatment with LPS or the substance, respectively.

An almost complete inhibition of Shwartzman-reaction is observed after pretreatment with LPS or test substance, respectively.

Furthermore, the compounds of formula Ia and III possess activity against tumors, as demonstrated in the following tests:

1. Induction of tumor necrosis factor (TNF)
2. B16F1 melanoma test

It is found that the compounds of the invention posses immunoprophylactic activity, which reflects in a reduction of the number of B16F1 melanoma metastases in the lungs. As a test of therapeutic activity, mice are treated on day 3, 6, 8, 10, 13 and 15 after inoculation of the tumor cells. Here, too, a marked reduction in the number of metastases is observed.

The description of the pharmacological test methods referred to above has been published in WO 87/00174 which is incorporated herein by reference.

The compounds of the invention are therefore useful as modulators of unspecific antimicrobial resistance, in the systemic enhancement of immune response, and in the enhancement of unspecific immunity. The compounds of the invention are thus useful in the treatment or supportive treatment (i.e. together with other specific or supportive therapeutic forms) of conditions associated with decreased immune response, especially decreased humoral immune response and/or decreased over-sensitivity reaction of the delayed type, and in the treatment of conditions in which generally a modulation of immune response is indicated. In particular, the compounds of the invention are useful in the treatment or supportive treatment of pathological conditions based on idopathic immunological deficiencies or immunological deficiencies of the type encountered in geriatric patients, or in patients with heavy burns or generalized infections. The compounds of the invention are also useful in the treatment or supportive treatment of viral illnesses (such as disseminated Herpes, progressive smallpox and disseminated varicella diseases), of Morbus Hodgkin and other malignant tumors. Furthermore, the compounds of the invention are useful in the prevention of endotoxin shock, e.g. in accidents, burns, and surgical interventions, and as antiinflammatory agents.

For the above-mentioned uses the dosage will, of course, vary depending on the compound employed, mode of administration and treatment desired. In general satisfactory results are obtained when administered at a daily dosage, or as a unique administration for the achievement of an adjuvant effect, e.g. in supportive treatment, of from about 0.0015 mg/kg to about 1 mg/kg animal body weight. Administration is e.g. parenterally, preferably i.p. For the larger mammal an indicated total daily dosage is in the range of from about 0.1 mg to about 70 mg, conveniently given, in the case of a daily dosage, in divided doses 2 to 4 times a day in unit dosage form containing from about 0.025 to about 35 mg of the compounds admixed or in sustained release form. An indicated total single adjuvant dosage is in the range of up to 70 mg of the compounds.

In view of their immunomodulating activity the compounds of the invention are also useful as adjuvants in vaccines. For this use an indicated dosage is from about 0.5 mg to about 100 mg, preferably about 70 mg, administered on the day of vaccination with appropriately a repetition in the same dosage 2 to 4 weeks thereafter.

The invention thus provides a method for combatting illnesses and infections as described above, comprising administering a therapeutically effective amount of a compound of the invention to a subject in need of such treatment.

The invention further also provides pharmaceutical compositions comprising a compound of the invention in association with at least one pharmaceutical carrier or diluent, such compositions may be prepared in conventional manner, e.g. by mixing with conventional, pharmaceutically acceptable carriers or diluents. They may be prepared e.g. in the form of an injectable solution, or in liposomal form.

Particularly preferred in the abobe indications is the compound of Example 1.

The invention also provides the use of the compounds of the invention for the preparation of pharmaceutical compositions, comprising mixing a compound of the invention with a pharmaceutically acceptable carrier or diluent.

The invention further also provides the compounds of the invention for use as pharmaceuticals, in particular for use as immunomodulators, as antiviral agents and as antiinflammatory agents.

In the following Examples, which illustrate the invention and are not limitative, all temperatures are in degrees centigrade.

EXAMPLE 1

2-deoxy-2-[3-(R)-hydroxytetradecanamido]-3,4-di-O-[3-(R)-hydroxytetradecanoyl]-α-D-glucopyranose-1-phosphate $R_1$, $R_2$, $R_3$ = 3-(R)-hydroxytetradecanoyl 500 mg 2-[3-(R)-benzytetradecanamido]-3,4-di-O-[3-(R)-benzyloxytetradecanoyl]-2-deoxy-6-O-triphenylmethyl-α-D-glucopyranose-1-dibenzyl phosphate are dissolved in 150 ml of tetrahydrofuran/water 4:1 and the resultant mixture is hydrogenated under normal pressure for 12 hours with 500 mg palladium on charcoal. The reaction mixture is filtered and again hydrogenated with 500 mg palladium on charcoal; this operation is repeated two more times (reaction time: 48 hours). The catalyst is filtered off, the tetrahydrofuran is distilled off, the aqueous suspension diluted with 10 ml water and lyophilized. The title compound is obtained:

$R_f=0.4$ (in chloroform/methanol/water/acetic acid 80:25:5:5

$[\alpha]_D^{20} = +22°$ (c=0.1 in chloroform/methanol 3:1).

The mono-tris(hydroxymethyl)aminomethane salt is also obtained.

The starting material is obtained as follows:

a) To a solution of 2 g 2-[3-(R)-benzyloxytetradecanamido]-2-deoxy-6-O-triphenylmethyl-D-glucopyranose in 270 ml of absolute tetrahydrofuran chilled to −60° are added 2.55 ml of a 1.6M solution of butyllithium in hexane. After 5 minutes a solution of 1.21 g dibenzylphosphorochloridate in 4 ml benzene is added dropwise at the same temperture as above. Agitation is maintained for 20 minutes at −60°, the pH is adjusted to 7 and the solvent evaporated to dryness. The residue is chromatographed without delay (toluene/acetic ester 1:1). 2-[3-(R)-Benzyloxytetradecanamido]-2-deoxy-6-O-triphenylmethyl-α-D-glucopyranose-1-dibenzyl phosphate is obtained ($R_f=0.47$ in toluene/acetic ester 1:1).

b) To a solution of 1.1 g of the compound obtained as described under a), 1 g 3-(R)-benzyloxytetradecanoic acid and 40 mg of 4-dimethylaminopyridine in 20 ml of dry dichloromethane chilled to 0° are added 619 mg dicyclohexylcarbodiimide. After 30 minutes the reaction mixture is brought to room temperature, after 4 hours the solution is filtered and the solvent evaporated. The residue is chromatographed in toluene/acetic ester 4:1. 2-[3-(R)-Benzyloxytetradecanamido]-3,4-di-O-[3-(R)-benzyloxytetradecanoyl]-2-deoxy-6-O-triphenylmethyl-α-D-glucopyranose-1-dibenzyl phosphate is obtained ($R_f=0.75$ in toluene/acetic ester 4:1).

EXAMPLE 2

2-deoxy-2-[3-(R)-hydroxytetradecanamido]-3-O-[3-(R)-hydroxytetradecanoyl]-4-O-tetradecanoyl-α-D-glucopyranose-1-phosphate $R_1$, $R_2$=3-(R)-hydroxytetradecanoyl; $R_3$=tetradecanoyl The title compound ($R_f$0.45 in chloroform/methanol/water/acetic acid 80:25:5:5) is obtained as described in Example 1, starting from 2-[3-(R)-benzyloxytetradecanamido]3-O-[3-(R)-benzyloxytetradecanoyl]-2-deoxy-4-O-tetradecanoyl-6-O-triphenylmethyl-α-D-glucopyranose-1-dibenzyl phosphate.

The starting material is obtained as follows:

a) 2.58 g imidazol and 5.03 g 1,3-dichloro-1,1,3,3-tetraisopropyl-disiloxane are stirred for 4 hours at 10° in 65 ml of dimethylformamide. The solution is added dropwise at −10° and under argon to a solution of 5.45 g 2-deoxy-2-[3-(R)-benzyloxytetradecanamido]-D-glucopyranose in 150 ml of dimethylformamide. After 90 minutes about 3 ml of methanol are added, the dimethylformamide is distilled off, the residue taken up in dichloromethane/water, the organic phase dried and distilled off. The residue is chromatographed in toluene/acetic ester 2:1. 2-[3-(R)-Benzyloxytetradecanamido]-2-deoxy-4,6-O-(1,1,3,3-tetraisopropyl-disiloxanyliden)-D-glucopyranose is obtained ($R_f=0.8$ in toluene/acetic ester 1:1).

b) The compound obtained as described under a) above is reacted with butyllithium and dibenzylphosphorochloridate as described in Example 1 a). 2-[3-(R)-Benzyloxytetradecanamido]-2-deoxy-4,6-O-(1,1,3,3-tetraisopropyldisiloxanyliden)-α-D-glucopyranose-1-dibenzyl phosphate is obtained ($R_f=0.6$ in toluene/acetic ester 1:1).

c) The compound obtained as described under b) above is reacted with 3-(R)-benzyloxytetradecanoic acid as described in Example 1 b). 2-[3-(R)-Benzyloxytetradecanamido]-3-O-[3-(R)-benzyloxytetradecanoyl]-2-deoxy-4,6-O-(1,1,3,3-tetraisopropyl-disiloxanyliden)-α-D-glucopyranose-1-dibenzyl phosphate is obtained ($R_f=0.6$ in toluene/acetic ester 4:1).

d) To a solution chilled to −20° of 800 mg of the compound obtained as described under c) above in 4 ml of dry tetrahydrofuran is slowly added dropwise 168 ml of tetrabutylammonium fluoride in tetrahydrofuran, followed 30 minutes later by 6 μl of acetic acid. The cold reaction mixture is then diluted with 25 ml of dichloromethane and extracted with 20 mg water. The organic phase is dried and evaporated. 2-[3-(R)-Benzyloxytetradecanamido]-3-O-[3-(R)-benzyloxytetradecanoyl]-2-deoxy-α-D-glucopyranose-1-dibenzyl phosphate is obtained without further purification ($R_f=0.6$ in toluene/acetic ester 3:2).

e) 600 mg of the compound obtained as described under d) above are dissolved into 13 ml of dry dichloromethane and 312 mg trityl chloride and 290 μl of N,N-diisopropylethylamine are added at room temperature. After 18 hours the solvent is distilled off and the residue chromatographed in toluene/acetic ester 4:1. 2-[3-(R)-Benzyloxytetradecanamido]-3-O-[3-(R)-benzyloxytetradecanoyl]-2-deoxy-6-O-triphenylmethyl-α-D-glucopyranose-1-dibenzyl phosphate is obtained ($R_f=0.6$ in toluene/acetic ester 4:1).

f) To a solution of 400 mg of the compound obtained as described under e) above, 69 mg tetradecanoic acid and 10 μg 4-dimethylaminopyridine in 7 ml of dry dichloromethane are added at room temperature 62 mg N,N-dicyclohexylcarbodiimide. After 20 hours the reaction mixture is filtered, the solvent distilled off and the residue chromatographed in toluene/acetic ester 5:1. 2-[3-(R)-Benzyloxytetradecanamido]-3-O-[3-(R)-benzyloxytetradecanoyl]-2-deoxy-4-O-tetradecanoyl-6-O-triphenylmethyl-α-D-glucopyranose-1-dibenzyl phosphate is obtained ($R_f=0.75$ in toluene/acetic ester 4:1)

EXAMPLE 3

2-deoxy-2-[3-(R)-hydroxytetradecanamido]-3,4-di-O-[3-(R)-tetradecanoyloxytetradecanoyl]-α-D-glucopyranose-1-phosphate $R_1$=3-(R)-hydroxytetradecanoyl; $R_2$, $R_3$=3-(R)-(tetradecanoyloxy)tetradecanoyl The title compound ($R_f$ 0.5 in chloroform/methanol/water 10:3:0.1) is obtained as described in Example 1, starting from 2-[3-(R)-Benzyloxytetradecamido]-2-deoxy-3,4-di-O-[3-(R)-tetradecanoyloxytetradecanoyl]-α-D-glucopyranose-1-dibenzyl phosphate.

The starting material is obtained as follows:

a) A solution of 2-[3-(R)-benzyloxytetradecanamido]-2-deoxy-6-O-triphenylmethyl-α-D-glucopyranose-1-dibenzyl phosphate, 3-(R)-tetradecanoyloxytetradecanoic acid and 4-dimethylaminopyridine in dichloromethane is reacted with dicyclohexylcarbodiimide as described in Example 1 b). 2-[3-(R)-Benzyloxytetradecanamido]-2-deoxy-3,4-di-O-[3-(R)-tetradecanoyloxytetradecanoyl]-6-O-triphenylmethyl-α-

D-glucopyranose-1-dibenzyl phosphate is obtained ($R_f$=0.5 in toluene/acetic ester 9:1).

b) 700 mg of the compound obtained as described under a) above are dissolved into 200 ml of diethyl ether and 2.5 ml of formic acid are slowly added dropwise. The reaction mixture is neutralized after 2 hours reaction time with saturated sodium hydrogen carbonate solution. The aqueous phase is separated off and the organic phase washed once with 2 ml of water. The organic phase is dried over magnesium sulfate and evaporated off. The residue is chromatographed over silicagel using toluene/acetic ester 4:1 as an eluent. 2-[3-(R)-Benzyloxytetradecanamido]-2-deoxy-3,4-di-O-[3-(R)tetradecanoyloxytetradecanoyl[-α-D-glucopyranose 1-dibenzyl phosphate is obtained ($R_f$=0.4 in toluene/acetic ester 4:1).

In a first group of compounds of the invention $R_1$, $R_2$ and $R_3$ are identical.

In a second group $R_1$, $R_2$ and $R_3$ are different.

In a 3rd group $R_1$ and $R_2$ are identical and $R_3$ is different from $R_1$ and $R_2$.

In a 4th group $R_2$ and $R_3$ are identical and $R_1$ is different from $R_2$ and $R_3$.

I claim:

1. The compound which is 2-deoxy-2-[3-(R)-hydroxytetradecanamido]-3,4-di-O-[3-(R)-hydroxytetradecanoyl]-α-D-glucopyranose-1-phosphate in free form or in salt form.

2. The compound which is 2-deoxy-2-[3-(R)-hydroxytetradecanamido]-3-O-[3-(R)-hydroxytetradecanoyl]-4-O-tetradecanoyl-α-D-glucopyranose-1-phosphate in free form or in salt form.

3. The compound which is 2-deoxy-2-[3-(R)-hydroxytetradecanamido]-3,4-di-O-[3-(R)-tetradecanoyloxytetradecanoyl]-α-D-glucopyranose-1-phosphate in free form or in salt form.

4. A pharmaceutical composition comprising a therapeutically effective amount of a compound selected from the group consisting of:

a) 2-deoxy-2-[3-(R)-hydroxytetradecanamido]-3,4-di-O-[3-(R)-hydroxytetradecanoyl]-α-D-glucopyranose-1-phosphate;

b) 2-deoxy-2-[3-(R)-hydroxytetradecanamido]-3-O-[3-(R)-hydroxytetradecanoyl]-4-0-tetradecanoyl-α-D-glucopyranose-1-phosphate; and c) 2-deoxy-2-[3-(R)-hydroxytetradecanamido]-3,4-di-O-[3-(R)-tetradecanoyloxytetradecanoyl]-α-D-glucopyranose-1-phosphate in free form or in salt form and a pharmaceutical carrier or diluent therefore.

* * * * *